United States Patent [19]

Szántay et al.

[11] Patent Number: 4,753,948
[45] Date of Patent: Jun. 28, 1988

[54] FURFURYL DERIVATIVES OF VINBLASTINE-TYPE BIS-INDOLES, AND PHARMACEUTICAL COMPOSITIONS CONTAINING THEM

[75] Inventors: Csaba Szántay; Lajos Szabó; Katalin Honty; Tibor Keve; Tibor Acs; Sandor Eckhardt; Janos Sugar; Zsuzsa Somjai; Eva Ivan; Zsuzsa Kneffel, all of Budapest, Hungary

[73] Assignee: Richter Gedeon Vegyeszeti Gyar R.T., Budapest, Hungary

[21] Appl. No.: 873,525

[22] Filed: Jun. 12, 1986

[30] Foreign Application Priority Data

Jun. 12, 1985 [HU] Hungary .............................. 2301/85

[51] Int. Cl.⁴ .................. A61K 31/475; C07D 519/04
[52] U.S. Cl. ..................................... 514/283; 540/478
[58] Field of Search ........................ 540/478; 514/283

[56] References Cited

U.S. PATENT DOCUMENTS 3,392,173  7/1968  Hargrove ........................... 540/478
4,298,525  11/1981  Jovánovics et al. ................. 540/478
4,410,459  10/1983  Dancsi et al. ....................... 540/478

Primary Examiner—Donald G. Daus
Assistant Examiner—Diana G. Rivers
Attorney, Agent, or Firm—Keil & Weinkauf

[57] ABSTRACT

The invention relates to novel furfuryl derivatives of the general formula (I),

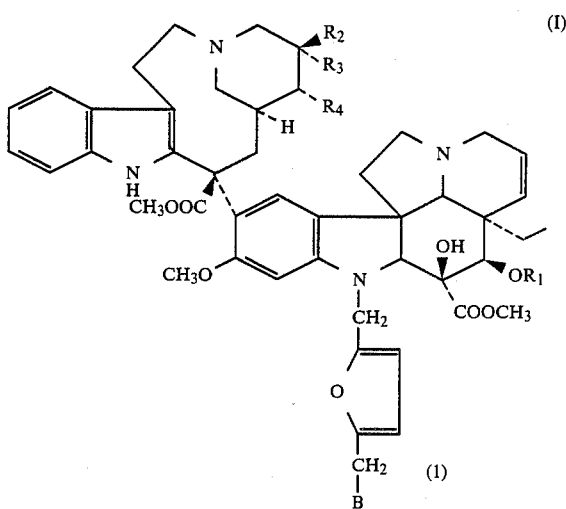

wherein
$R_1$ stands for a hydrogen atom or an acetyl group,
$R_2$ stands for a hydroxyl or ethyl group of $\beta$-position;
$R_3$ means an ethyl group of $\alpha$-position;
$R_4$ represents a hydrogen atom; or
$R_3$ and $R_4$ together represent an oxygen bridge; and
B stands for a hydroxyl of an O-acyl group, as well as their acid addition salts and pharmaceutical preparations containing these compounds. Further on, the invention relates to a process for preparing these compounds and preparations.

The compounds of the general formula (I) show a cytostatic activity with less toxicity than that of the commerically available known vinblastine-type bis-indole alkaloid drugs.

4 Claims, No Drawings

FURFURYL DERIVATIVES OF VINBLASTINE-TYPE BIS-INDOLES, AND PHARMACEUTICAL COMPOSITIONS CONTAINING THEM

The invention relates to novel furfuryl derivatives of vinblastine-type bis-indoles of the formula (I),

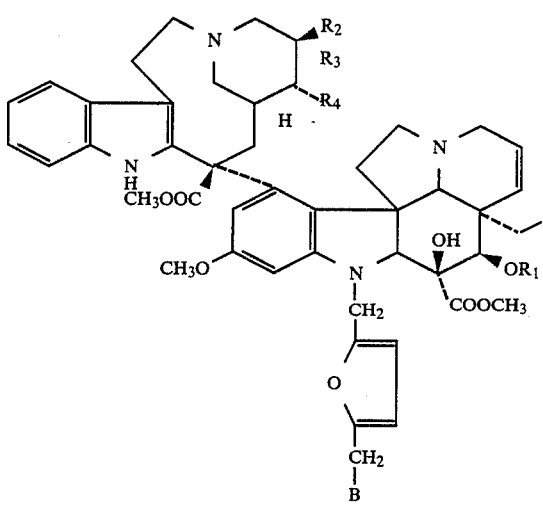

wherein
$R_1$ stands for a hydrogen atom or an acetyl group;
$R_2$ stands for a hydroxyl or ethyl group of $\beta$-position;
$R_3$ means an ethyl group of $\alpha$-position;
$R_4$ represents a hydrogen atom; or
$R_3$ and $R_4$ together represent an oxygen bridge; and
B stands for a hydroxyl or an O-acyl group, as well as their acid addition salts and pharmaceutical preparations containing these compounds.

According to an other aspect of the invention, there is provided a process for the preparation of the new compounds of the formula (I) and their acid addition salts.

It is known that according to the Hungarian patent specifications Nos. 181,745 and 181,746 (which correspond respectively to U.S. Pat. Nos. 4,410,459 and 4,490,378) the O,$N_a$-acetals of vinblastine-type bis-indole alkaloids can be brought into an acetal-interchange reaction with an appropriate nucleophilic reagents. These patents disclose that a $CH_2$—O—R group (where R is alkyl) can be formed on the nitrogen atom 1 in position 1 of bis-indoles of the vinblastine-type by oxidation or by acetal re-arrangement. The oxidation can take place in the presence of chromium trioxide, a suitable organic solvent, acetic anhydride and an acid, at a temperature between $-60°$ C. and $-30°$ C., wherein the pH of the reaction mixture is adjusted to 8 to 10 and the product is isolated. The various S,$N_a$-acetals of bis-indoles have been prepared by using the same method (see the Hungarian patent application No. 2303/85) which corresponds to U.S. application Ser. No. 873,540. In the process disclosed in the application a—CH—OR group (wherein R stands for an alkyl group) attached to the nitrogen atom of position 1 of vinblastine-type alkaloids is transformed with an —R—SH compound into a —$CH_2$—SR compound.

Now it has been found that this reaction takes a course different from the expected one when furfuryl alcohol is used in the acetal-interchange reaction under suitably selected reaction conditions. Namely, according to our observations, when a furfuryl derivative of the formula (III),

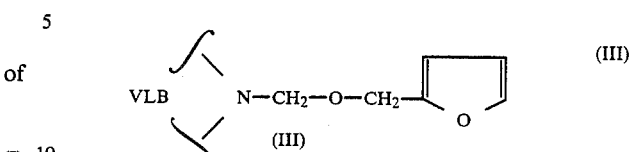

obtained from a compound of the formula (IIa) under mildly acidic reaction conditions,

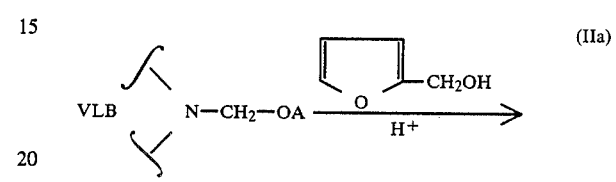

is reacted with an excess of furfuryl alcohol in a strongly acidic medium, then an α-aminomethylated furan derivative is obtained, wherein the $N_a$-nitrogen of the bis-indole dimer is present as amino nitrogen. The compounds of the formula (Ia)

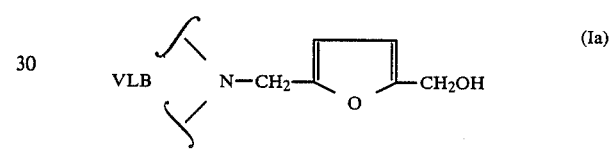

prepared in the manner described above fall within the scope of the compounds of the general formula (I). These reaction steps are illustrated in Reaction Scheme 1.

It has also been stated that the previous separation of the O,$N_a$-acetal formed with the furfuryl alcohol [e.g. separation of the compound of formula (III)] is not necessary for obtaining the compounds of the formula (I). According to the Reaction Scheme 2, the desired furfuryl derivative may directly be prepared from any O,$N_a$— or S,$N_a$—acetal.

Reaction scheme 1

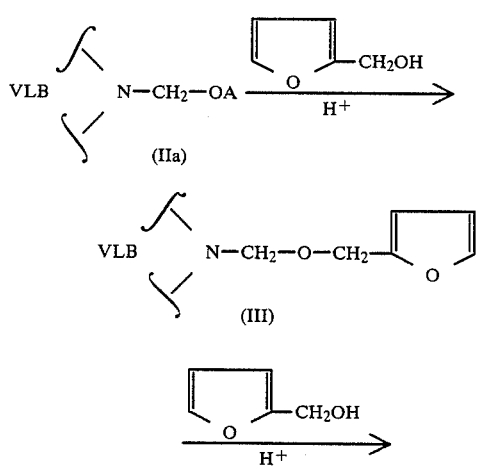

-continued
Reaction scheme 1

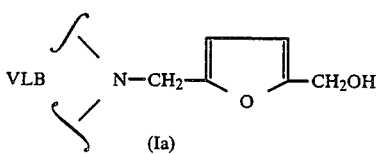

Reaction scheme 2

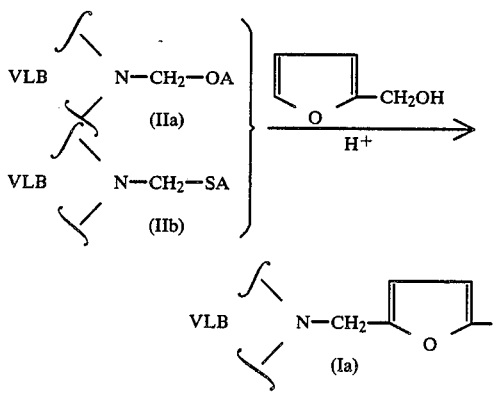

Based on these facts, there is provided a process for preparing the compounds of the formula (I), wherein $R_1$, $R_2$, $R_3$, $R_4$ and B are the same as defined above, and their acid addition salts, which comprises (a) reacting a compound of the formula (II),

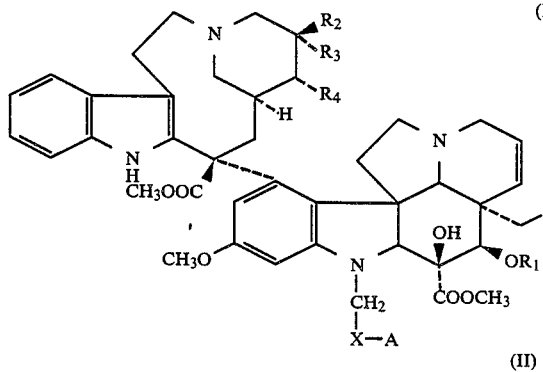

wherein $R_2$, $R_3$ and $R_4$ are the same as defined above;
X means a sulphur or an oxygen atom; and
A stands for an optionally usubstituted alkyl, aralkyl, cycloalkyl or a heteromatic group,
with furfuryl alcohol in the presence of a mineral acid or a Lewis acid in a solvent, preferably in a halogenated hydrocarbon, then working up the reaction mixture and isolating the desired product, or (b) transforming a compound of the formula (I), wherein $R_1$ stands for an acetyl group;
$R_2$ stands for a hydroxyl or ethyl group of $\beta$-position;
$R_3$ represents an ethyl group of $\alpha$-position;
$R_4$ means a hydrogen atom; or
$R_3$ and $R_4$ together represent an oxygen bridge; and
B stands for a hydroxyl group,
by using a simple chemical operation, preferably a deacetylation or acylation, thus changing the meaning of $R_1$ and B, then isolating the thus-obtained product and, if desired, transforming the thus-obtained product to an acid addition salt thereof.

The compounds of the formula (I) show a cytostatic activity with less toxicity than that of the known vinblastine-type bis-indole alkaloid drugs which are commercially available.

For investigating the biological activity, the injectable solutions containing water-insoluble compounds to be tested were dissolved by using physiological saline solution and one drop of Tween-80 each. These solutions were intraperitoneally administered in a volume of 0.1 ml/10 g of body-weight.

The effect of the novel compounds of intraperitoneally transplantable tumours (P388 mouse leukaemia) is reported hereinafter.

The P388 leukaemia was maintained in DBA/2 inbred mice and transplanted intraperitoneally by administering $10^6$ tumour cells/animal to groups consisting of 6 BDF$_1$ hybride mice each. In the 24th hour following the transplantation, the daily intraperitoneal treatment with the novel compounds was started. The body-weight and condition of the animals were daily controlled. The effect achieved on the animals treated for 8 days was expressed as the percentage of the mean survival time in days of the control group (T/C %).

It is obvious from Table 1 that the compounds investigated are capable to significantly extend the life span of P388 leukaemic mice within a defined dose range.

The most important advantage of the compounds of the invention is that in the course of and after 8 times repeated administration of the effective doses, the paralyses of the hind limbs and of the bladder, which are observed on using vincristine and indicate neurotoxic effects, do not appear.

According to a preferred embodiment of the process of the invention, the compounds of the formula (I) are prepared as follows:

TABLE 1

| Compound | Effect T/C %+ | | | | | | |
|---|---|---|---|---|---|---|---|
| | 0.1 | 0.2 | 0.4 | 1.0 | 2.0 | 4.0 | 8.0 |
| | | | | mg/kg | | | |
| N—Demethyl-N—(4-hydroxymethyl-furfuryl)-vinblastine | — | — | 146 | 187 | 198 | 228 | 202 |
| 17-Deacetyl-N—demethyl-N—(4-hydroxy-methylfurfuryl)-vinblastine | — | — | 132 | 133 | 141 | 181 | 186 |
| Vincristine | 203 | 186 | 207 | (0.6 is toxic) | | | |

+The effect is expressed as the percentage of the mean survival time of the control group On carrying out the process (a), the starting compound of the formula (II) is dissolved in a solvent. Suitable solvents are ethers, ketones, benzene or its homologues as well as dimethyl formamide. Chlorinated hydrocarbons such as dichloromethane, chloroform and carbon tetrachloride are the most preferred solvents.

As catalyst a mineral acid, preferably hydrochloric or sulphuric acid, or Lewis acids may be used in this reaction. It is suitable to adjust the pH of the reaction mixture to a value lower than 3.

The process of the invention is carried out most preferably at room temperature, but the reaction may in general be realized at a temperature between $-20°$ C. and $+20°$ C.

On carrying out the process (b), a compound of the formula (I) is used as starting material which contains an acetyl group in 17-position or in which B represents a hydroxyl group. Namely, in the latter case, the terminal hydroxyl group permits the possibility of further transformations (e.g. acylation).

After carrying out the above reactions, the product is separated from the reaction mixture by means of extraction and/or evaporation and optionally purified by using a chromatographic method and/or recrystallization. The chromatography is performed on a silica gel column.

The compounds used as starting materials in process (a) are known. Derivatives of N-demethyl-N-alkoxymethylvinblastine and -leurosine are described in the Hungarian patent specification No. 181,745 (which corresponds to U.S. Pat. No. 4,410,459); the thio derivatives are reported in the Hungarian patent application No. 2303/85 (which corresponds to U.S. application Ser. No. 873,540).

The compounds used as starting materials in the process (b) are novel and they are prepared according to the process (a) of the invention.

The invention is illustrated in detail by the aid of the following non-limiting Examples.

EXAMPLE 1

Preparation of N-demethyl-N-(4-hydroxymethylfurfuryl)-vinblastine (A) Preparation of N-demethyl-N-furfuryloxymethylvinblastine 1.5 ml (17 mmoles, about 50 equivalents) of furfuryl alcohol are added to a solution containing 300 mg (0.36 mmole) of N-methoxymethylvinblastine in 40 ml of abs. dichloromethane at 0° C., then the pH value of the mixture is acidified to 5 to 6 by slowly adding abs. ethereal hydrogen chloride solution. The course of the reaction is followed by thin layer chromatography (TLC) (by using a 20:1.5 mixture of developing system of dichloromethane and methanol; the $R_f$ value of the product is higher than that of the starting substance). At the end point of the reaction the acidic solution is neutralized by adding saturated potassium carbonate solution (2 to 3 ml), the organic layer is washed twice with 5 ml of water each, dried and evaporated under reduced pressure. The residue is triturated twice with 5 ml of petroleum ether each and purified by column chromatography under the following conditions.

Adsorbent: silica gel with a particle size of 0.04–0.063 mm.

Column: 20 mm in diameter, 190 mm in height; in dichloromethane.

Dissolving and washing: dichloromethane, 10+50 ml.

Development: with 100 ml of a mixture containing 1% of methanol in dichloromethane.

Elution: with 600 ml of a mixture containing 3% of methanol in dichloromethane.

TLC: with a solvent system containing a 2:20 mixture of methanol and dichloromethane.

The repeated purification of the product may be achieved on $Al_2O_3$ II-III adsorbent by using dichloromethane and dichloromethane containing 1% of methanol, respectively. Thus, the aimed product is obtained in a yield of 150 mg (46%), m.p.: 218°–221° C. (amorphous);

$[\alpha]_D = +38°$ (c=1, chloroform).

$C_{51}H_{62}N_4O_{11}$ (molecular weight: 906).

IR (KBr, $cm^{-1}$): 740, 930, 1040, 1220–1260, 1380, 1470, 1505, 1620, 1730, 2950, 3450.

(B) Transformation of N-demethyl-N-furfuryl-oxymethylvinblastine to N-demethyl-N-(4-hydroxymethylfurfuryl)-vinblastine 30 μl of furfuryl alcohol are added to a solution containing 10 mg of N-demethyl-furfuryl-oxymethylvinblastine in 2 ml of abs. dichloromethane at room temperature, then the pH value is adjusted to 3 by adding abs. ethereal hydrogen chloride solution. According to the TLC analysis, the reaction proceeds instantaneously. Under anhydrous conditions, the thus-obtained product is free from side-products. After the common working-up of column chromatography 6 mg of the aimed product are obtained, m.p.: 190°–194° C. (amorphous); $[\alpha]_D = -4°$ (c=1, chloroform).

$C_{51}H_{62}N_4O_{11}$ (molecular weight 906).

IR (KBr, $cm^{-1}$): 740, 1030, 1010, 1200–1260, 1375, 1460, 1500, 1510, 1730, 2950, 3400.

EXAMPLE 2

Preparation of N-demethyl-N-(4-hydroxymethylfurfuryl)-vinblastine 2.55 ml (29 mmoles, 30 equivalents) of furfuryl alcohol are added to a solution containing 830 mg (0.98 mmole) of N-demethyl-N-(methoxymethyl)-vinblastine in 65 ml of abs. dichloromethane, then the pH of the solution is adjusted to about 3 by adding abs. ethereal hydrogen chloride solution. The course of the reaction is followed by TLC (by using a developing system of a 20:2 mixture of dichloromethane and methanol; the $R_f$ value of the product is lower than that of the starting material). At the end point of the reaction the acidic solution is neutralized by adding saturated potassium carbonate solution (2 to 3 ml), the mixture is diluted with water and after separating the phases, the aqueous layer is extracted 3 times with 20 ml of dichloromethane each. The combined organic phase is washed 3 times with 20 ml of water each, dried over anhydrous magnesium sulphate and evaporated under reduced pressure. The excess of the reagent is removed from the crude product by triturating 3 times with 15 ml of petroleum ether each and the oily residue is purified by column chromatography under the following conditions:

Adsorbent: silica gel with a particle size of 0.04–0.063 mm.

Column: 20 mm in diameter, 190 mm in height; in dichloromethane.

Dissolving and washing: dichloromethane, 10+100 ml.

Development: with 200 ml of a mixture containing 0.5% of methanol in dichloromethane.

Elution: with 200 ml of a mixture containing 1% of methanol in dichloromethane, then with 400 ml of a mixture containing 3% of methanol in dichloromethane; and finally with 400 ml of a mixture containing 5% of methanol in dichloromethane.

TLC: with a solvent system consisting of a 2:20 mixture of methanol and dichloromethane.

By using the above process, 680 mg of the aimed product are obtained, the physical properties of which are in accordance with those of the compound prepared in Example 1.

EXAMPLE 3

Preparation of N-demethyl-N-(4-hydroxymethylfurfuryl)-vinblastine hydrochloride

A solution containing 20 mg of N-demethyl-N-(4-hydroxymethylfurfuryl)-vinblastine in 1 ml of dichloromethane is acidified by adding abs. ethereal hydrogen chloride solution. The hydrochloride is precipitated by adding 2 ml of a 1:1 mixture of abs. ether and petroleum. The thus-obtained substance is amorphous without any characteristic melting point.

EXAMPLE 4

Preparation of N-demethyl-N-(4-hydroxymethylfurfuryl)-leurosine

A solution containing 0.5 g (0.6 mmoles) of N-methoxymethylleurosine and 1.3 ml (0.1 mmole, 25 equivalents) of furfuryl alcohol in 30 ml of abs. dichloromethane is acidified to pH 3 by adding abs. ethereal hydrogen chloride solution. The course of the reaction is followed by TLC (by using a developing system of a 20:2 mixture of dichloromethane and methanol; the $R_f$ value of the starting material is higher than that of the product). At the end point of the reaction the acidic solution is neutralized by adding saturated potassium carbonate solution. The solution is diluted with water and after separation of the phases, the aqueous layer is extracted three times with 20 ml of dichloromethane each. The combined organic phase is washed with water, dried over anhydrous magnesium sulphate and evaporated under reduced pressure. The thus-obtained crude product is purified by column chromatography under the following conditions:

Adsorbent: silica gel with a particle size of 0.063–0.2 mm.
Column: 20 mm in diameter, 150 mm in height; in dichloromethane.
Dissolving and washing: dichloromethane, 20+50 ml.
Development: with 200 ml of a mixture containing 0.5% of methanol in dichloromethane.
Elution: with 200 ml of a mixture containing 1% of methanol in dichloromethane; with 400 ml of a mixture containing 3% of methanol in dichloromethane; and with 300 ml of a mixture containing 5% of methanol in dichloromethane.
TLC: with a solvent system containing a 2:20 mixture of methanol and dichloromethane.

By using the above process, 399 mg (74%) of the aimed product are obtained.
IR (KBr, cm$^{-1}$): 730, 1020, 1200–1240, 1320, 1360, 1450, 1495, 1605, 1730, 2900, 3400.

EXAMPLE 5

Preparatioon of N-demethyl-N-(4-hydroxymethylfurfuryl)-vinblastine from N-demethyl-N-(2-acetoxyethylthiomethyl)-vinblastine 250 μl (2.5 mmoles, 40 equivalents) of furfuryl alcohol are added to a solution containing 60 mg (60 μmoles) of the starting material in 50 ml of abs. dichloromethane. The solution is cooled to 0° C. and acidified to pH 2 by adding abs. ethereal hydrogen chloride solution. The course of the reaction is followed by TLC (by using a developint system of a 20:2 mixture of dichloromethane and methanol; the $R_f$ value of the starting material is higher than that of the product). At the end point of the reaction the acidic solution is neutralized by adding potassium carbonate solution. The solution is washed twice with 5 ml of water each, dried over anhydrous magnesium sulphate and evaporated under reduced pressure. The thus-obtained product is purified by column chromatography under the following conditions:

Adsorbent: silica gel with a particle size of 0.04–0.063 mm.
Column: 12 mm in diameter, 140 mm in height; in dichloromethane.
Dissolving and washing: dichloromethane, 10+50 ml.
Development: with 100 ml of a mixture containing 1% methanol in dichloromethane;
Elution: with 100 ml of a mixture containing 3% of methanol in dichloromethane; with 200 ml of a mixture containing 5% of methanol in dichloromethane.
TLC: with a solvent system containing a 2:20 mixture of methanol and dichloromethane.

By using the above process, 40 mg (74%) of the aimed product are obtained, the physical properties of which are in agreement with those of the compound prepared in Example 1.

EXAMPLE 6

Preparation of N-demethyl-N-(4-acetoxymethylfurfuryl)-leurosine

A solution containing 200 mg (0.23 mmole) of N-(4-hydroxymethylfurfuryl)-leurosine, 480 mg (4 mmoles, 20 equivalents) of 4-dimethylaminopyridine and 1.2 ml (50 equivalents) of acetic anhydride in 20 ml of abs. dichloromethane is let to stand for 3 hours at room temperature. The course of the reaction is followed by TLC (by using a developing system of a 20:2 mixture of dichloromethane and methanol; the $R_f$ value of the product is higher than that of the starting substance). At the end point of the reaction, the solution is diluted with 30 ml of dichloromethane and 20 ml of water and alkalized to pH 9 by adding concentrated ammonium hydroxide solution. After separating the phases the organic layer is washed three times with 15 ml of water each, dried over anhydrous magnesium sulphate and evaporated under reduced pressure. The product is made free from the excess reagent by column chromatography to give the aimed product in a yield of 0.16 g (70%).

EXAMPLE 7

Preparation of 17-deacetyl-N-demethyl-N-(4-hydroxymethylfurfuryl)-vinblastine 250 mg (0.28 mmole) of N-demethyl-N-(4-hydroxymethylfurfuryl)-vinblastine are dissolved in 10 ml of 0.5N sodium methoxide solution and set aside at room temperature for 8 hours. (The course of the reaction is followed by TLC by using a developing system of a 20:2 mixture of dichloromethane and methanol; the $R_f$ value of the starting material is higher than that of the product). At the end point of the reaction, the base is neutralized by adding 0.3 ml (50 mmoles) of glacial acetic acid and the solution is evaporated under reduced pressure. The residue is dissolved in 40 ml of dichloromethane, washed twice with 15 ml of water each, dried and again evaporated. In this way 213 mg of a crude product are obtained which is subjected to column chromatography under the following conditions:

Adsorbent: silica gel with a particle size of 0.04–0.063 mm.

Column: 20 mm in diameter, 100 mm in height; in dichloromethane.

Dissolving and washing: dichloromethane, 15+50 ml.

Development: with 50 ml of a mixture containing 1% of methanol in dichloromethane.

Elution: with 100 ml of a mixture containing 3% of methanol in dichloromethane; with 200 ml of a mixture containing 5% of methanol in dichloromethane; with 200 ml of a mixture containing 7% of methanol in dichloromethane.

TLC: with a solvent system containing a 3:20 mixture of methanol and dichloromethane.

By using the above process, 160 mg (65%) of the aimed product are obtained; m.p.: 158°–162° C. (amorphous); $[\alpha]_{546} = +18°$ (c=1, chloroform).

$C_{49}H_{60}N_4O_{10}$ (molecular weight: 864).

IR (KBr, cm$^{-1}$): 740, 1020, 1140, 1220–1260, 1470, 1505, 1620, 1730, 2920, 3400.

We claim:

1. Furfuryl derivatives of vinblastine-type of bisindoles of the formula (I),

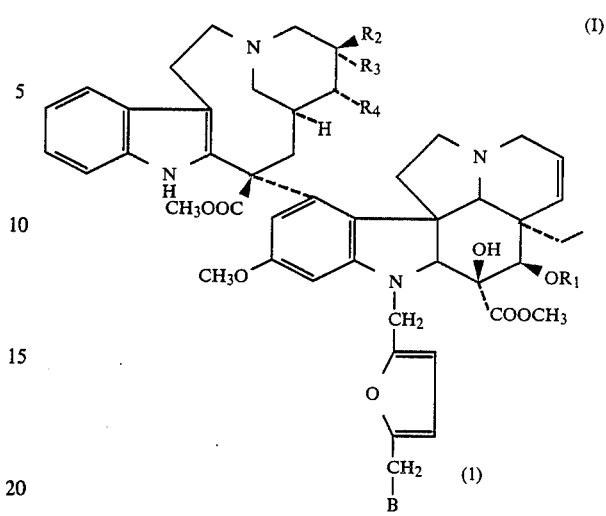

wherein
$R_1$ is a hydrogen atom or an acetyl group;
$R_2$ is hydroxyl or β-ethyl;
$R_3$ is an α-ethyl;
$R_4$ is a hydrogen atom; or
$R_3$ and $R_4$ together represent an oxygen bridge; and
B is hydroxyl or an O-acyl group,
as well as their pharmaceutically acceptable acid additional salts.

2. A compound as defined in claim 1 selected from the group consisting of
N-demethyl-N-(4-hydroxymethylfurfuryl)-vinblastine,
N-demethyl-N-(4-hydroxymethylfurfuryl)-leurosine,
N-demethyl-N-(4-acetoxymethylfurfuryl)-leurosine and
17-deacetyl-N-demethyl-N-(4-hydroxymethylfurfuryl)-vinblastine
as well as the hydrochlorides of these compounds.

3. A pharmaceutical composition having cytostatic activity which comprises an effective amount of a furfuryl derivative of the formula I as defined in claim 1, or a pharmaceutically acceptable acid addition salt thereof and a pharmaceutically acceptable carrier and/or diluent.

4. A pharmaceutical composition having cytostatic activity which comprises an effective amount of a furfuryl compound as defined in claim 2, or a pharmaceutically acceptable acid addition salt thereof and a pharmaceutically acceptable carrier and/or diluent.

* * * * *